US005478831A

United States Patent [19]

Furrer et al.

[11] Patent Number: 5,478,831

[45] Date of Patent: Dec. 26, 1995

[54] R-(−)1-(5-HYDROXYHEXYL)-3-METHYL-7-PROPYLXANTHINE, A PROCESS FOR ITS PREPARATION AND PHARMACEUTICALS CONTAINING THIS COMPOUND

[75] Inventors: Harald Furrer, Hofheim am Taunus; Ulrich Gebert, Schlossborn; Karl Rudolphi, Neu-Isenburg, all of Germany

[73] Assignee: Hoechst Aktiengesellschaft, Frankfurt am Main, Germany

[21] Appl. No.: 241,717

[22] Filed: May 12, 1994

Related U.S. Application Data

[62] Division of Ser. No. 631,415, Dec. 21, 1990, Pat. No. 5,407,815.

[30] Foreign Application Priority Data

Dec. 23, 1989 [DE] Germany .......................... 39 42 871.0

[51] Int. Cl.$^6$ ......................... C07D 473/06; A61K 31/52

[52] U.S. Cl. ............................................ 514/263; 544/267

[58] Field of Search .................................... 544/266, 267; 514/263

[56] References Cited

U.S. PATENT DOCUMENTS

| | | |
|---|---|---|
| 4,108,995 | 8/1978 | Mohler et al. . |
| 4,515,795 | 5/1985 | Hinze et al. . |
| 4,576,947 | 3/1986 | Hinze et al. . |

FOREIGN PATENT DOCUMENTS

| | | |
|---|---|---|
| 0198440 | 10/1986 | European Pat. Off. . |
| 0272605 | 6/1988 | European Pat. Off. . |
| 2236501 | 2/1975 | France . |
| 2366527C2 | 8/1987 | Germany . |
| 3942872 | 12/1989 | Germany . |

OTHER PUBLICATIONS

Davis, P. J., et al., Mircobial Models of Mammalian Metabolism: Stereospecificity of Ketone Reduction with Pentoxifylline, Xenobiotica, vol. 15, No. 12, 1985, pp. 1001–1010.

Merete Ruud–Christensen et al., Separation of (R)–And (S)–proxyphylline As Diastereoisomeric Camphantes By Reversed–phase Liquid Chromotography, Journal of Chromatography 303 (1984) pp. 433–435.

Davis, P. J., et al., Microbial Models of Mammalian Metabolism: Microbial Reduction and Oxidation of Pentoxifyline, Applied and Environmental Microbiology, Aug. 1984, pp. 327–331, vol. 48, No. 2.

Merete Ruud–Christensen et al., Synthesis of (R)–and (S)–proxyphylline, 1984 Acta Chemica Scandinavica.

M. Christen et al., J. Chem Soc., Chem Comm. 264–44 (1988).

ATCC Catalogue of Yeasts at 71 (18th Ed., 1990).

*Primary Examiner*—Nicholas Rizzo

*Attorney, Agent, or Firm*—Finnegan, Henderson, Farabow, Garrett & Dunner

[57] ABSTRACT

R-(−)-1-(5-Hydroxyhexyl)-3-methyl-7-propylxanthine, a process for its preparation, and pharmaceuticals which contain this compound and which are suitable, in particular, for the prophylaxis and treatment of cerebral vascular disorders.

3 Claims, No Drawings

R-(−)1-(5-HYDROXYHEXYL)-3-METHYL-7-PROPYLXANTHINE, A PROCESS FOR ITS PREPARATION AND PHARMACEUTICALS CONTAINING THIS COMPOUND

This is a division of application Ser. No. 07/631,415, filed Dec. 21, 1990, now U.S. Pat. No. 5,407,815.

It is known that the racemic compound 1-(5-hydroxyhexyl)-3-methyl-7-propylxanthine has, inter alia, a cerebral blood flow-stimulating action (DE-C-2,366,527). The formula of the compound is:

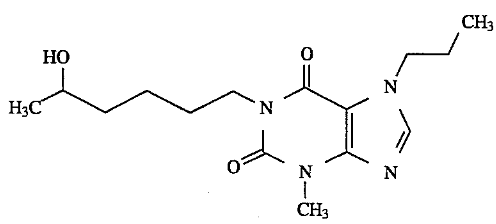

The carbon atom carrying the hydroxyl group in the hydroxyhexyl side chain is asymmetric. However, nothing has yet been reported about corresponding enantiomers.

If the cerebral blood flow-stimulating action of the racemate is made equal to 1, one of the two enantiomeric compounds—the S-(+)-enantiomer—has a value of about 0.65. A value of about 1.35 was therefore to be expected for the other enantiomeric compound—the R-(−)-enantiomer. Surprisingly, however, the value for the R-(−)-enantiomer is about 2. This means that the cerebral blood flow-stimulating action of the R-(−)-enantiomer is about three times as strong as that of the S-(+)-antipode; the duration of action of the R-(−)-compound is also about three times the duration of action of the S-(+)-compound.

The present invention therefore relates to the R-(—)-compound.

The R-(−)-compound can be prepared by several methods.

One process comprises, for example, the introduction of the 5-hydroxyhexyl radical already having the R configuration into the 1-position of 3-methyl-7-propylxanthine by known procedures;

but resolution of the racemate into the antipodes by known standard methods is also possible.

A further preparation possibility is the stereoselective synthesis of 1-(5-oxohexyl)-3-methyl-7-propylxanthine; stereoselective reduction with the aid of microorganisms is preferred in this case.

A process of this type is described in German Patent Application P 39 42 872.9 (HOE 89/F 405), filed at the same time. This process comprises stereospecifically reducing 1-(5-oxohexyl)-3-methyl-7-propylxanthine using the yeast strain Rhodotorula rubra (which was deposited in the German Collection of Microorganisms and Cell Cultures on 10.7.1989 under the number DSM 5436), S-(+)-1-(5-hydroxyhexyl)-3-methyl-7-propylxanthine being formed, which is then subjected to an inversion of configuration.

According to another preferred microbial process, a) 1-(5-oxohexyl)-3-methyl-7-propylxanthine is stereoselectively reduced using baker's yeast (Saccharomyces cerevisiae; manufacturer: Deutsche Hefewerke GmbH, Frankfurt/Main) to S-(+)-1-(5-hydroxyhexyl)-3-methyl-7-propylxanthine, which is then in turn subsequently b) subjected to an inversion of configuration.

The reduction with baker's yeast is expediently carried out between room temperature and about 40° C., preferably in the presence of sucrose, in general at pH values of about 7 to 8.5 in water or in mixtures of water with water-miscible—in this case inert—organic solvents such as ethanol, ethylene glycol or dimethylformamide, it being possible for the reaction time to extend from a few hours to several days.

The subsequent inversion of configuration of the S-(+)- to the R-(−)-enantiomer is advantageously carried out using a tertiary phosphine (preferably triphenylphosphine), an organic carboxylic acid (preferably benzoic acid) and a dialkyl azodicarboxylate (preferably diethyl azodicarboxylate)

in an aprotic solvent (preferably in tetrahydrofuran) in general at temperatures between about 20° to about 30° C., and the carboxylic acid ester of the R-(−)-enantiomer formed in this case is then cleaved by solvolysis according to known processes in alcoholic or aqueous solvents in the presence of basic substances, in particular by methanolysis in the presence of potassium carbonate. The solvolysis product is then worked up in a known manner.

The inversion of configuration can also be carried out in a similarly advantageous manner by converting the S-(+)-enantiomer (1) into the corresponding sulfonic acid ester using a sulfonyl halide, if appropriate in the presence of a base, in an aprotic solvent, (2) reacting this ester with an alkali metal salt of an aliphatic carboxylic acid in an aprotic solvent to give the corresponding carboxylic acid ester, whereupon the inversion of configuration takes place, and (3) liberating the compound as claimed in claim 1 from this carboxylic acid ester by solvolysis in an alcoholic or aqueous solvent in the presence of a basic substance.

In step (1) it is preferred to employ methanesulfonyl chloride or p-toluenesulfonyl chloride as the organic sulfonyl halide, triethylamine as the base and pyridine and/or dichloromethane as the aprotic solvent; the preferred alkali metal salt of an aliphatic carboxylic acid—in step (2)—is cesium propionate and the preferred aprotic solvent in this step is dimethylformamide and/or dimethyl sulfoxide. This step is in general carried out at temperatures between about 20° and 100° C. in the course of a few hours up to several days. Methanol is preferably used as solvent for the solvolysis (step (3)) and potassium carbonate as a preferred basic substance in this step.

The invention furthermore relates to pharmaceuticals which contain R-(−)-1-(5-hydroxyhexyl)-3-methyl-7-propylxanthine.

The pharmaceuticals are suitable in particular for the prophylaxis and treatment of cerebral vascular disorders.

The pharmaceuticals according to the invention can be administered orally, rectally or parenterally.

Suitable solid or liquid pharmaceutical preparation forms are, for example, granules, powders, tablets, coated tablets, (micro)capsules, suppositories, syrups, emulsions, suspensions, drops or injectable solutions and preparations having a sustained release of active compound, in whose production auxiliaries, such as excipients, disintegrants, binders, coating agents, swelling agents, glidants or lubricants, flavorings, sweeteners or solubilizers are customarily used. Frequently used auxiliaries are, for example, lactose, mannitol and other sugars, talc, lactoprotein, gelatin, starch, cellulose and its derivatives, animal and vegetable oils, polyethylene glycols, and solvents, such as, for example, sterile water.

The following example is intended to illustrate the preparation of the compound according to the invention after which an experimental report then follows, from which can be seen the surprisingly increased cerebral blood flow-stimulating action and the favorable duration of action of this compound.

EXAMPLE a) Microbial reduction of 1-(5-oxohexyl)-3-methyl-7 -propylxanthine to S-(+)-1-(5-hydroxyhexyl)-3-methyl-7-propylxanthine 1200 g of sucrose and 840 g of baker's yeast (Goldhefe, Deutsche Hefewerke GmbH) in 6.5 l of water are stirred at 30°–35° C. After 1 h, 184 g of 1-(5-oxohexyl)-3-methyl-7-propylxanthine are added dropwise in the course of 10 minutes, a further 1200 g of sucrose and 840 g of baker's yeast in 5.5 l of water are added after 24 hours, and a a further 800 g of sucrose are added after a further 24 hours and the mixture is stirred for 8 hours more.

1.8 kg of celite are stirred into the suspension, and it is filtered through a pressure filter and washed with isopropanol. The filtrates are combined, concentrated to about 2 l under reduced pressure and worked up by extraction with dichloromethane and water. The dichloromethane phase is dried and concentrated under reduced pressure. The residue is purified by column chromatography on silica gel (eluents: dichloromethane/ethanol, volume ratios: 98:2) and by bulb tube distillation at 0.1 mbar and a bath temperature of 140°–145° C.

Yield: 21.7 g Melting points 81°–82° C. Enantiomeric purity: >95% $[\alpha]_D^{20}$ =+4.6° (c=6.7, $C_2H_5OH$)

Analysis: Calc: C 58.42% H 7.84% N 18.17% Founds C 58.50% H 7.95% N 18.19% b) Inversion of configuration of S-(+)- to R-(−)-1-(5 -hydroxyhexyl)-3-methyl-7-propylxanthine A solution of 10.9 g of diethyl azodicarboxylate in 60 ml of anhydrous tetrahydrofuran is added dropwise at 20°–25° C. to a mixture of 18.5 g of S-(+)-(5-hydroxyhexyl)-3 -methyl-7-propylxanthine, 7.3 g of benzoic acid and 16.1 g of triphenylphosphine in 60 ml of anhydrous tetrahydrofuran.

After stirring at 20°–25° C. for 24 h, the mixture is concentrated under reduced pressure, the residue is purified by column chromatography on silica gel (eluent: dichloromethane/ethanol, volume ratio: 95:5) and 50.5 g of crude R-1-(5-benzoyloxy)-3-methyl-7-propylxanthine are obtained. This is heated at reflux temperature in 750 ml of methanol together with 4 g of potassium carbonate for 32 h and the mixture is concentrated under reduced pressure. After working up the residue by extraction with dichloromethane and water, 48.5 g of crude product are obtained after concentrating the dried dichloromethane phase and are purified by column chromatography on silica gel (eluent: dichloromethane/ethanol, volume ratio: 95:5→90:10) and bulb tube distillation at a bath temperature of 140° C. and 0.1 mbar.

Yield: 13.9 g Melting point: 81°–82° C. $[\alpha]_D^{20}$=−4.5° (c=6.4, $C_2H_5OH$) Enantiomeric purity >95%

Analysis: Calc.: C 58.42% H 7.84% N 18.17% Found: C 58.35% H 8.05% N 18.36%

The structure of the compounds was checked by elemental analysis and IR and H-NMR spectra. The absolute configuration and enantiomeric purity were determined by means of the Mosher ester using S-(−)-methoxytrifluoromethylphenylacetic acid ($^1$H- or $^{19}$F-NMR spectra). The enantiomeric purity was additionally also determined by gas chromatography after derivatization with S-(−)-1-phenylethyl isocyanate.

Experimental report:

Cerebral blood flow of the cat

The action of compound 1 according to the invention on the regional cerebral blood flow was investigated in comparison with the racemate 2 and the S-(+)-enantiomer 3 with the aid of the heat conductivity technique according to F. A. Gibbs (Proc. Soc. exp. Biol. (New York) 31 (1933), pp. 141 et seq.), H. Hensel (Naturwissenschaften 43 (1956), pp. 477 et seq.) and E. Betz (Acta Neurol. Scand. Suppl. 14 (1965), pp. 29–37) in cats of both sexes under sodium pentobarbital anesthesia (35 mg/kg i.p.). In this method, with the aid of a heat conductivity probe applied to the surface of the brain in the region of the Gyrus marginalis frontalis, the transport of heat from a point of heating to an adjacent temperature-measuring site in the probe, which is directly proportional to the level of the cerebral blood flow, is determined. The mean percentage change in the heat transport number $\lambda$ after administration of the preparation is used as a measure of the increase in blood flow.

The compounds were administered intraduodenally as a suspension in 1% strength aqueous carboxymethylcellulose. The dose was 25 mg of test substance per kg of body weight. 6 to 11 individual experiments were carried out for each test preparation and the mean percentage change in the heat transport number ($\Delta\lambda\%$) was determined from the measurement data obtained.

The melting points m.p., the enantiomeric purities e.e. (enantiomeric excess), the number of measurements n, the mean percentage change ($\Delta\lambda\%$) of the heat transport number as a measure of the potency, the conversion factors f, based on $\Delta\lambda\%$ =1 for the racemate, and the duration of action as the half life $t_{1/2}$ (min) for R-(−)-1-(5-hydroxyhexyl)-3-methyl-7-propylxanthine (1), the corresponding enantiomer S-(+)-1-(5-hydroxyhexyl)-3-methyl-7-propylxanthine (3) and the racemate (2) of the two compounds is indicated in Table 1.

TABLE 1

| | Change in the cerebral blood flow | | | | | |
|---|---|---|---|---|---|---|
| Compound | m.p. | e.e. | n | Δ λ % | (f) | $t_{1/2}$ (min) |
| 1(R-(−)) | 81-82° C. | >95% | 6 | +45 | (1.88) | 100 |
| 2(Rac.) | 76-77° C. | — | 7 | +24 | (1.00) | 100 |
| 3(S-(+)) | 81-82° C. | >95% | 11 | +16 | (0.67) | 36 |

We claim:

1. R-(−)-1-(5-Hydroxyhexyl)-3-methyl-7-propylxanthine.

2. A pharmaceutical which contains R-(−)-1-(5-hydroxyhexyl)-3-methyl-7-propylxanthine.

3. A method for the prophylaxis or treatment of cerebral vascular disorders comprising administering to a host in need of said prophylaxis or treatment an effective amount of the compound of claim 1.

* * * * *